(12) United States Patent
Oka et al.

(10) Patent No.: US 6,437,199 B1
(45) Date of Patent: Aug. 20, 2002

(54) METHOD FOR PRODUCTION OF HIGH-PURITY MONOETHYLENE GLYCOL

(75) Inventors: Yoshihisa Oka, Chigasaki; Yutaka Sugiyama, Yokohama; Kenji Suzuki, Yokohama; Hironori Horie, Yokohama; Makoto Furukawa, Zushi, all of (JP)

(73) Assignee: Nippon Shokubai Co., Ltd., Osaka (JP)

( * ) Notice: Subject to any disclaimer, the term of this patent is extended or adjusted under 35 U.S.C. 154(b) by 0 days.

(21) Appl. No.: 09/615,504

(22) Filed: Jul. 13, 2000

(30) Foreign Application Priority Data

Jul. 14, 1999 (JP) .......................................... 11-200898
Jul. 14, 1999 (JP) .......................................... 11-200899

(51) Int. Cl.$^7$ .......................... C07C 27/00; C07C 27/26
(52) U.S. Cl. ...................... 568/867; 568/866; 568/868; 568/872
(58) Field of Search ................................ 568/868, 872, 568/866, 867

(56) References Cited

U.S. PATENT DOCUMENTS

| 3,904,656 A | | 9/1975 | Broz | 260/348.5 R |
| 3,964,980 A | * | 6/1976 | Ozero | 260/348.5 R |
| 4,349,417 A | * | 9/1982 | Rebsdat et al. | 203/33 |
| 4,647,705 A | * | 3/1987 | Schmitt et al. | 568/868 |
| 5,124,004 A | * | 6/1992 | Grethlein et al. | 203/19 |

FOREIGN PATENT DOCUMENTS

| JP | 61-3772 | 2/1986 | ........... C07C/31/20 |

* cited by examiner

*Primary Examiner*—Samuel Barts
*Assistant Examiner*—Elvis O. Price
(74) *Attorney, Agent, or Firm*—Fish & Richardson P.C.

(57) ABSTRACT

A method for the production of monoethylene glycol of high purity is disclosed which comprises subjecting ethylene to catalytic vapor phase oxidation with a molecular oxygen-containing gas thereby obtaining an ethylene oxide-containing gas, exposing the ethylene oxide-containing gas to an absorbing solution and stripping the resultant ethylene oxide-containing solution in a stripper, condensing the vapor emanating from the top of the stripper thereby obtaining crude ethylene oxide, subjecting at least part of the crude ethylene oxide to a hydration reaction, adding an alkaline substance to the hydration reaction solution in an amount of not less than 0.5 atomic equivalent weight relative to the chlorine atom contained in the hydration reaction solution or dehydrating the hydration reaction solution and introducing the side cut technique to the monoethylene glycol rectification column, and acquiring the monoethylene glycol from the side cut part.

12 Claims, 3 Drawing Sheets

METHOD FOR PRODUCTION OF HIGH-PURITY MONOETHYLENE GLYCOL

BACKGROUND OF THE INVENTION

1. Field of the Invention

This invention relates to a method for the production of high-purity monoethylene glycol. More particularly, it relates to a method for producing a high-purity monoethylene glycol possessing a fiber-grade quality and excelling in thermal stability by using as the raw material for a hydration reaction an unpurified crude ethylene oxide obtained during the course of producing and purifying ethylene oxide by catalytic vapor phase oxidation of ethylene with a molecular oxygen-containing gas in the presence of a silver catalyst.

2. Description of the Prior Art:

Among the conventional methods for producing ethylene glycol by using as the raw material for a hydration reaction an unpurified crude ethylene oxide obtained during the course of manufacture of ethylene oxide by catalytic vapor phase oxidation of ethylene with a molecular oxygen-containing gas in the presence of a silver catalyst, there have been counted (1) a method which as described in JP-B-61-3,772 comprises condensing the vapor emanating from the top of an ethylene oxide stripper in two condensers, refluxing the condensate to the stripper, forwarding the uncondensed gas to a third condenser and condensing the gas therein, forwarding the resultant condensate to a hydration reaction vessel, and carrying out a reaction of conversion to glycol, (2) a method which as described in U.S. Pat. No. 3,904,656 comprises guiding a gas emanating from the top of a stripper to a reabsorption column, performing therein absorption of the gas with an absorbing liquid having water as a main component thereof, forwarding the absorbing liquid having absorbed ethylene oxide to a hydration reaction vessel, and carrying out a reaction of the absorbing liquid, and (3) a method which as described in U.S. Pat. No. 3,964,980 comprises condensing the gas arising from the top of a stripper by a condenser, returning the condensate as reflux to the stripper, guiding the uncondensed gas to a reabsorption column to be absorbed therein, guiding the absorption liquid having absorbed the produced ethylene oxide to a hydration reaction vessel to be subjected to reaction therein.

U.S. Pat. No. 4,349,417 discloses a method for the production of high-purity monoethylene glycol, characterized by adding an aqueous alkalimetal compound solution to the reaction product between a hydration reaction vessel and a monoethylene glycol rectification column adapted to distil monoethylene glycol through the top thereof and effecting this addition of the reaction product in an amount such that the reaction product, while entering the monoethylene glycol rectification column, assumes a pH value in the range of 7–10. In U.S. Pat. No. 4,349,417 mentioned above, in disclosing the invention, makes no mention of the fact that the ethylene oxide (crude ethylene oxide) as the raw material for the hydration reaction incorporates such organic chlorine compounds as ethylene dichloride and ethylene chlorohydrin as extraneous matter. It discloses absolutely no knowledge concerning the technical problem which arises from the use of the raw material for the hydration reaction containing such organic chlorine compounds and the measure for the solution thereof.

We have proposed as in JP-B-61-3,772 a method for producing high-purity monoethylene glycol by using as the raw material for a hydration reaction the unpurified crude ethylene oxide obtained during the course of manufacture of ethylene oxide by catalytic vapor phase oxidation of ethyene with a molecular oxygen-containing gas. This method implements the manufacture of monoethylene glycol without requiring addition of an alkali because the process involved therein has no need for consideration about a measure to cope with the organic chloride compounds arising from the chlorine compound in the crude ethylene oxide.

No method has been heretofore proposed to date which produces high-purity monoethylene glycol by using as the raw material for a hydration reaction an unpurified crude ethylene oxide containing organic chloride compounds. Such is the true state of prior art.

When the hydration reaction is carried out with the liquid which is obtained by condensing the gas arising from the top of an ethylene oxide stripper, refluxing the condensate, and cooling or absorbing the uncondensed gas as contemplated by the conventional method, the ethylene oxide obtained from the uncondensed gas at the first stage does not include most of chloride compounds because the chlorine compounds migrate into the condensate at the first stage or to the bottoms of the column. It may well be concluded, therefore, that the ethylene glycol to be obtained by hydrating this ethylene oxide contains such chlorine compounds only in an amount deserving to be called "trace."

We, not satisfied with the prior art and with a view to further simplifying the process for the production of monoethylene glycol and saving the energy consumed therein, have studied the feasibility of using as the raw material for the hydration reaction the unpurified crude ethylene oxide obtained without refluxing the top of an ethylene oxide stripper during the manufacture of ethylene oxide by catalytic vapor phase oxidation of ethylene with a molecular oxygen-containing gas in the presence of a silver catalyst. We have consequently found that when the unpurified crude ethylene oxide is used as the raw material for the hydration reaction, the monoethylene glycol product consequently obtained offers no sufficient stability to withstand the heating and could not afford a fiber grade product.

Specifically, during the manufacture of ethylene oxide by catalytic vapor phase oxidation of ethylene with a molecular oxygen-containing gas in the presence of a silver catalyst, such organic chloride compounds as ethylene dichloride and ethylene chlorohydrin emanate from the top of an ethylene oxide stripper in conjunction with ethylene oxide and the like. It has been found that notwithstanding such organic chlorine compounds are removed by a subsequent operation of separation by distillation, the monoethylene glycol obtained by using the condensate obtained from the gas emanating from the top of the ethylene oxide stripper in its unmodified form as the raw material for the hydration reaction is destined to entrain as a foreign matter the chlorine compounds in an amount corresponding to 10–20% of the organic chlorine compounds which are present in the raw material for the hydration reaction.

We, therefore, have made a diligent study with a view to elucidating the cause for this persistent adulteration of the monoethylene glycol and have been consequently ascertained that the monoethylene glycol as a finished product has such qualities as thermal stability degraded because the inorganic chlorine originating in the organic chlorine compounds such as ethylene dichloride which are contained in the unpurified crude ethylene oxide (which are added during the process for the production of ethylene oxide by catalytic vapor phase oxidation of ethylene with a molecular oxygen-containing gas in the presence of a silver catalyst) emerges in the hydration reaction solution and, consequently, such impurities as ethylene chlorohydrin are formed during the process of dehydration of ethylene glycol and are suffered to mingle as foreign matter into the rectified monoethylene glycol.

We have studied from various angles the process for the production of monoethylene glycol with a view to simplifying the process of production, saving the energy spent therein, and reducing the cost of production and have been consequently ascertained that in the conventional technique for producing monoethylene glycol by using as the raw material for the hydration reaction of purified ethylene oxide, the objects mentioned above are accomplished by changing the raw material for the hydration reaction from purified ethylene oxide to unpurified crude ethylene oxide but that this measure not merely fails to bring a sufficient reduction in the concentration of heavy aldehyde, particularly glycol aldehyde, which is entrained by the crude ethylene oxide, formed by the reaction of hydration, and brought eventually into the monoethylene glycol product to stay therein but also degrades the thermal stability of the monoethylene glycol as a finished product. This degradation of the thermal stability is considered to be caused not only by the glycol aldehyde but also by the impurities (such as, for example, ethylene chlorohydrin and diethylene glycol monochlorohydrin) which occur when organic chlorine compounds, aldehydes, and organic acids entering the site of process owing to the use of the crude ethylene oxide are varied during the hydration reaction and completed through the reaction of monoethylene glycol with a substance having a boiling point approximating closely thereto or during the course of the rectification of monoethylene glycol by distillation.

An object of this invention, therefore, is to provide a method for the production of high-purity monoethylene glycol which succeeds in simplifying the process and operation of the production, saving the energy to be spent in the production, and reducing the cost of the production, decreasing the glycol aldehyde content in the monoethylene glycol to be produced and, at the same time, decreasing the substances causing degradation of the thermal stability mentioned above, and satisfying the qualities required of the fiber grade high-purity monoethylene glycol.

Another object of this invention is to provide a method for the production of a high-purity monoethylene glycol which succeeds in simplifying the process and operation of the production, saving the energy to be spent in the production, repressing the inclusion of such impurities as ethylene chlorohydrin as foreign matter into the monoethylene glycol to be obtained as a product, and satisfying the product specifications required of a fiber grade high-purity monoethylene glycol.

Still another object of this invention is to provide a method for the production of a fiber grade high-purity monoethylene glycol product which, in spite of the use of an unpurified crude ethylene oxide containing chlorine compounds as the raw material for a hydration reaction, represses the inclusion of impurities as a foreign matter similarly to the monoethylene glycol product obtained by using purified ethylene oxide as the raw material for the hydrolygic reaction and manifests high thermal stability.

SUMMARY OF THE INVENTION

We have pursued a diligent study concerning methods for the production of high-purity monoethylene glycol with a view to accomplishing the objects mentioned above and have consequently discovered that by using unpurified ethylene oxide as the raw material for a hydration reaction thereby simplifying the process and operation of the production, saving the energy to be consumed in the production, and lowering the cost of production and, at the same time, adopting a very simple means of introducing the technique of side cut to a monoethylene glycol rectification column without additionally installing devices for the removal of impurities, improving such devices, and adding new steps, it is made possible unexpectedly to acquire from the side cut part a high-purity monoethylene glycol product containing glycol aldehyde at an extremely low concentration and manifesting high thermal stability and accomplish the simplification of the process and operation of the production, saving the economy to be spent therein, and lowering the cost of production fully satisfactorily as a whole. This invention has been perfected as a result.

We have continued a diligent study concerning methods for the production of high-purity monoethylene glycol with a view to accomplishing the objects mentioned above. We have consequently discovered that by using the chlorine compound-containing unpurified crude ethylene oxide obtained without refluxing the top of an ethylene oxide stripper as the raw material for a hydration reaction thereby promoting the saving of the energy to be spent in the reaction and, at the same time, fixing the inorganic chlorine arising from decomposition of part of an organic chlorine compound from an external source with an alkaline substance by extremely simple means without requiring installation of a complicate treatment or apparatus or increasing the number of steps greatly with respect to a new addition of impurities originating in the unpurified crude ethylene oxide and thereafter purifying the monoethylene glycol in a monoethylene glycol rectifying column, it is made possible to repress the formation of such an organic chlorine compound as ethylene chlorohydrin as an impure substance and prevent this defiling compound from mingling into the product. This invention has been perfected as a result.

The objects mentioned above are accomplished by a method for the production of monoethylene glycol of high purity, which comprises subjecting ethylene to catalytic vapor phase oxidation with a molecular oxygen-containing gas thereby obtaining an ethylene-containing gas, exposing the ethylene oxide-containing gas to an absorbing solution thereby obtaining an ethylene oxide-containing solution, stripping the ethylene oxide-containing solution in a stripper, condensing the vapor emanating from the top of the stripper thereby obtaining crude ethylene oxide, subjecting at least part of the crude ethylene oxide to a hydration reaction, adding an alkaline substance in an amount of not less than 0.5 atomic equivalent weight to the chlorine atom contained in the hydration reaction solution, and subjecting the resultant mixture to rectification.

The objects mentioned above are also accomplished by a method for the production of monoethylene glycol of high purity, which comprises subjecting ethylene to catalytic vapor phase oxidation with a molecular oxygen-containing gas thereby obtaining an ethylene-containing gas, exposing the ethylene oxide-containing gas to an absorbing solution thereby obtaining an ethylene oxide-containing solution, stripping the ethylene oxide-containing solution in a stripper, condensing the vapor emanating from the top of the stripper thereby obtaining crude ethylene oxide, subjecting at least part of the crude ethylene oxide to a hydration reaction, dehydrating the product of the hydration reaction, introducing the side cut technique to a monoethylene glycol rectification column, and acquiring monoethylene glycol from the side cut part.

The objects mentioned above are accomplished by a method for the production of monoethylene glycol of high purity, which comprises subjecting ethylene to catalytic vapor phase oxidation with a molecular oxygen-containing gas thereby obtaining an ethylene-containing gas, exposing the ethylene oxide-containing gas to an absorbing solution thereby obtaining an ethylene oxide-containing solution, stripping the ethylene oxide-containing solution in a stripper, condensing the vapor emanating from the top of the stripper thereby obtaining crude ethylene oxide, subjecting at least part of the crude ethylene oxide to a hydration reaction, adding an alkaline substance in an amount of not less than 0.5 atomic equivalent weight to the chlorine atom contained in the hydration reaction solution, dehydrating the product of the hydration reaction, introducing the side cut technique to a monoethylene glycol rectification column, and acquiring monoethylene glycol from the side cut part.

The method of this invention for the production of monoethylene glycol of high purity succeeds in simplifying a process and saving energy by using the unpurified crude ethylene oxide containing a chlorine compound as the raw material for a hydration reaction, preventing inorganic chlorine from reacting with ethylene glycol by adding an alkaline substance in a prescribed amount to the hydration reaction solution and consequently fixing the inorganic chlorine, exalting greatly the transmittance to the ultraviolet ray of the rectified monoethylene glycol after application of heat and acquiring a monoethylene glycol product of high purity of fiber grade enjoying high thermal stability by repressing the formation of an organic chlorine compound during the purification of monoethylene glycol.

Further, the method of production of this invention is economically at an advantage in only requiring the existing production facility to incorporate therein a line for the addition of the alkaline substance and making effective use of the production facility in its existing state.

This invention has another advantage of successfully economizing the process for the production of monoethylene glycol in terms of the consumption of energy (allowing more saving of the energy than when the top of the ethylene oxide stripper is refluxed) by using as the unpurified crude ethylene oxide at least one of the oxides, i.e. (1) the ethylene oxide in a condensate obtained by cooling and/or absorbing the ethylene oxide-containing vapor emanating from the top part of the ethylene oxide stripper thereby condensing the vapor partly or wholly, (2) extracting the condensate obtained by partly or wholly condensing the ethylene oxide-containing vapor emanating from the top part of the ethylene oxide stripper without refluxing the condensate to the stripper, and (3) the product obtained by partly condensing the ethylene oxide-containing vapor emanating from the top part of the ethylene oxide stripper thereby obtaining a first condensate, guiding the remaining uncondensed gas, either after being further condensed or in its unmodified state, to the ethylene oxide dehydration column, and mixing the resultant dehydrated ethylene oxide with the first-condensate mentioned above.

This invention accomplishes simplification of the process and operation of the production, reduction in the consumption of energy, and decrease of the cost of production by introducing the side cut technique to the monoethylene glycol rectification column and acquiring monoethylene glycol from the side cut part in producing monoethylene glycol by using the unpurified crude ethylene oxide as the raw material for the hydration reaction, permits such contaminants as glycol aldehyde and substances detrimental to thermal stability which have been separated with great difficulty from monoethylene glycol by the conventional treatment of distillation to be condensed from the top part of the monoethylene glycol rectification column and discharged from the system, represses to an exceptionally great extent the amount of such contaminants otherwise possibly suffered to mingle into ethylene glycol extracted from the side cut part. Thus, the produced monoethylene glycol enjoys extremely high purity and high yield and realizes a generous addition to value as a fiber grade product of high thermal stability.

EXPLANATION OF THE PREFERRED EMBODIMENTS

Figure 1:
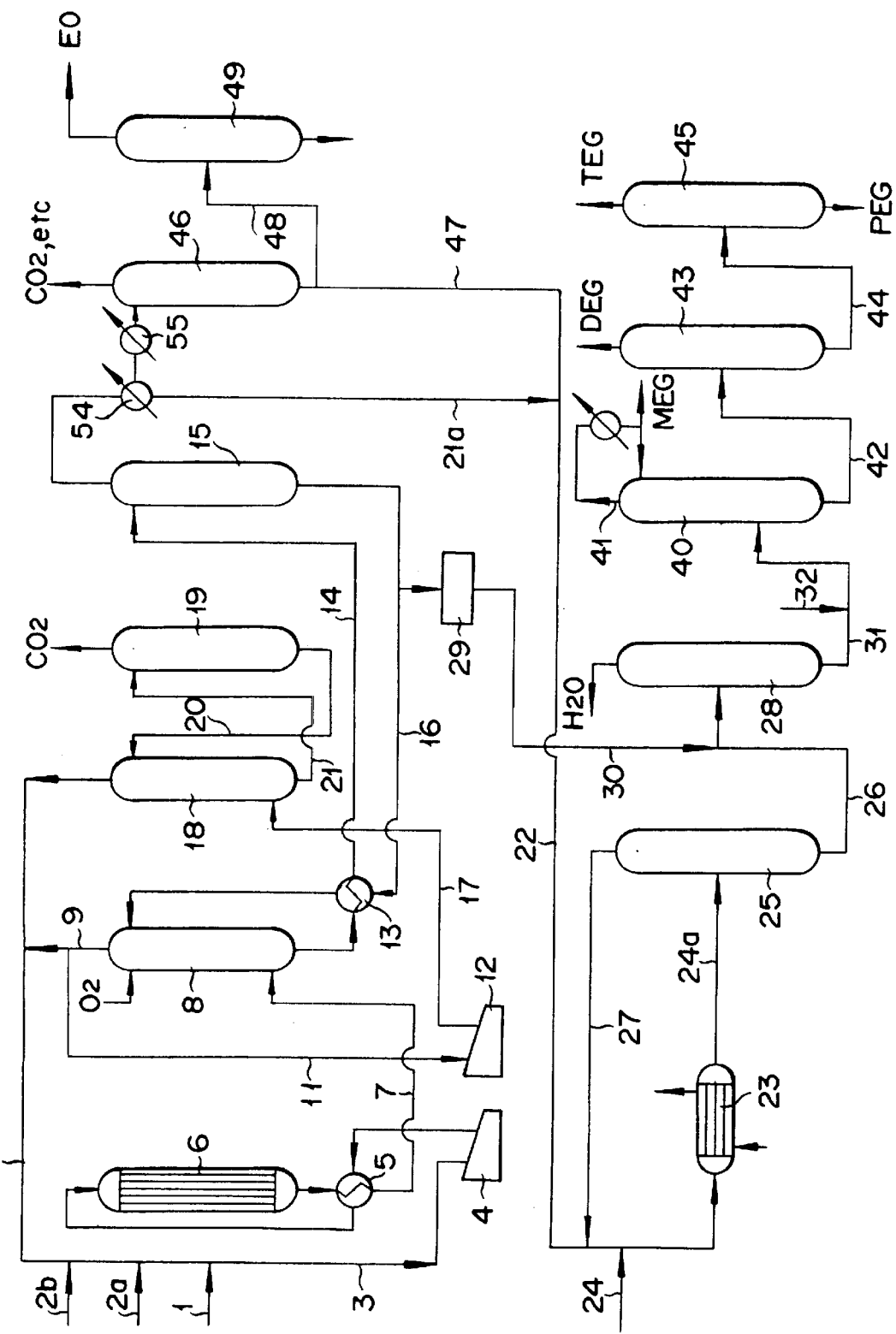
FIG. 1 is a flow sheet illustrating one example of the mode of embodying the method of this invention.

One example of the mode of embodying this invention will be explained below with reference to the drawings. First, ethylene, methane, and a chlorine compound (such as, for example, ethylene dichloride, ethyl chloride, methyl chloride, etc.) are supplied respectively through lines 1, 2a, and 2b and introduced jointly via a line 3 into a circulation gas compressor 4, compressed therein to a prescribed pressure, preheated in a heat exchanger 5, and then supplied to a reaction vessel 6 packed with a silver catalyst and subjected at a predetermined temperature to catalytic vapor phase oxidation. The reaction mixture gas is cooled in the heat exchanger 5 and then supplied via a line 7 to an absorption column 8 and brought into counter flow contact with an absorption solution (water) to absorb ethylene oxide. The molecular oxygen-containing gas and the unreacted ethylene are separated through the top of an ethylene oxide absorption column 8, with the result that part of the separated gas is circulated from a line 9 to the circulation gas compressor 4 via a line 10 and the remainder thereof is circulated to a circulation gas compressor 12 via a line 11.

The bottoms of the ethylene oxide absorption column 8 are preheated in a heat exchanger 13 and then supplied via a line 14 into an ethylene oxide stripper 15. The bottom of the ethylene oxide stripper 15 are advanced through a line 16, cooled in the heat exchanger 13, and then supplied as an absorption solution to the top of the ethylene oxide absorption column 8. The gas which has been compressed in the circulation gas compressor 12 is supplied via a line 17 to a carbon dioxide absorption column 18 and the absorption solution from the bottom of a carbon dioxide stripper 19 is advanced through a line 20 and supplied from the top of the carbon dioxide absorption column 18. The gases under discussion are brought into counter flow contact to effect absorption of carbon dioxide. The bottoms are supplied via a line to the carbon dioxide stripper 19. The carbon dioxide is consequently discharged through the top of the column.

The gas emanating from the top of the ethylene oxide stripper 15 is condensed by a condenser and then is partly or wholly supplied via lines 21a and 22 to an ethylene glycol reaction vessel 23 and, at the same time, subjected to a hydration reaction with the water supplied through a line 24. The reaction solution emanating from the ethylene glycol reaction vessel 23 is supplied via a line 24a to a concentration device 25 such as a multiple effect evaporator can and the water is circulated via a line 27 to the ethylene glycol reaction vessel 23. Meanwhile, the concentrated solution is supplied via a line 26 to a dehydration column 28. The bottoms of the ethylene oxide stripper 15 contain ethylene glycol. Part of the bottoms, when necessary, may be pretreated in a pretreatment device 29 and then supplied via a line 30 to the dehydration column 28.

The bottoms of the dehydration column 28 which contains practically no water and still contains a chlorine component, after adding an alkaline substance introduced via a line 32, are supplied via a line 31 to a monoethylene glycol rectification column 40. The gas emanating from the top of this column 40 is removed through a line 41 and condensed. Part of the condensed liquid is refluxed to the monoethylene glycol rectification column and the remainder thereof is acquired as a monoethylene glycol (MEG) product. The bottoms of the monoethylene glycol rectification column 40 are forwarded via a line 42 to a diethylene glycol rectification column 43. Through the top of this column 43, diethylene glycol DEG) is obtained. Further, the bottoms of the diethylene glycol rectification column 43 are supplied via a line 44 to a triethylene glycol rectification column 45. Triethylene glycol (TEG) is obtained from the top and polyethylene glycol is obtained from the bottom respectively of the column 45.

The crude ethylene oxide which is a part of obtained liquid by condensing the top gas of the ethylene oxide stripper 15 or re-condensed liquid of an uncondensed gas in the first condenser 54, when necessary, is further cooled by a cooler 55 and then is supplied to a light end stripper 46. After carbon dioxide and other light ends are removed through the top of this column, the crude ethylene oxide emanating from the bottom of the column may be supplied via lines 47 and 22 to the ethylene glycol reaction vessel 23. Part of the bottoms may be supplied via a line 48 to an ethylene oxide rectification column 49, with the result that ethylene oxide (EO) will be acquired through the top of the column and such contaminants as acetaldehyde will be removed through the bottom of the column.

The alkaline substance which can be used in this invention does not need to be particularly restricted but is only required to dissolve in water and exhibit basicity. Such basic salts as oxides, hydroxides, and carbonates of alkali metals and alkaline earth metals are preferred examples. As typical examples of the alkaline substance, therefore, hydroxides of alkali metals such as sodium hydroxide and potassium hydroxide, hydroxides of alkaline earth metals such as magnesium hydroxide and calcium hydroxide, and sodium carbonate and sodium hydrogen carbonate may be cited. Among other alkaline substances mentioned above, hydroxides of alkali metals and alkaline earth metals prove particularly favorable on account of high solubility in glycol. This invention permits these alkaline substances to be used singly or in the form of a mixture formed of two or more members at a proper ratio.

The amount of the alkaline substance to be added is only required to allow the residual chlorine in the hydration reaction solution to be properly fixed. The optimum amount for the addition may be properly selected, depending on the amount of the inorganic chlorine to be generated in the hydration reaction solution. The alkaline substance is added in an amount of not less than 0.5, preferably 0.5–2, and particularly preferably 0.5–1 atomic equivalent weight per atom of the inorganic chlorine generated in the hydration reaction solution. If the amount of the alkaline substance so added is less than 0.5 atomic equivalent weight per atom of the inorganic chlorine generated in the hydration reaction solution, it will be insufficient for solidifying fully satisfactorily the inorganic chlorine contained in the hydration reaction solution, particularly in the bottoms of the monoethylene glycol dehydration column, with the result that the unsolidified portion of the inorganic chlorine component will react with ethylene glycol in the monoethylene glycol purification column and the ethylene chlorohydrin formed consequently will mingle into the monoethylene glycol product. When the monoethylene glycol product is heated, therefore, it inevitably forms methyl dioxolane in the presence of ethylene glycol and ethylene chlorohydrin possibly to the extent of degrading the transmittance to the ultraviolet ray after application of heat. Conversely, if the amount of the alkaline substance exceeds 2 atomic equivalent weights per atom of the inorganic chlorine suffered to occur in the hydration reaction solution, the added alkaline substance will permit fully satisfactory solidification of the inorganic chlorine in spite of the use of a hydroxide of a monovalent alkali metal. In this respect, the excess addition of the alkali substance poses no problem. The excess of the alkaline substance, however, fails to bring a proportional addition to the effect drived from the addition and entails such an economic disadvantage as increasing the amount of water during the separation of the excess alkaline substance. Incidentally, this addition of the alkaline substance results in heightening the pH value of the hydration reaction solution. Since the composition of the hydration reaction solution varies its composition with the time for the addition of the alkaline substance, the pH value of the hydration reaction solution after the addition of the alkaline substance cannot be uniquely defined. Though the pH value is raised to a level in the approximate range of 5–9, It suffices to control this pH value in the range of 5–7.

The amount of the inorganic chlorine in the hydration reaction solution can be accurately determined by such a method of determination as ion chromatography, for example.

The form of the alkaline substance to be assumed for the sake of addition does not need to be particularly restricted. The alkaline substance may be in a solid form or a liquid form, whichever suits the occasion. When the alkaline substance is added through the line leading from the bottom part of the ethylene glycol dehydration column to the monoethylene glycol rectification column, the addition of this substance in the form of an aqueous solution does not prove proper. The use of this alkaline substance in the form of an alkali solution diluted to a proper concentration with monoethylene glycol of high purity may well be regarded as commendable from the viewpoint of allowing easy handling and facilitating mixture in addition to repressing the amount of water suffered to mingle as foreign matter into the product.

The method for the production of monoethylene glycol of high purity by the use of the construction of apparatus in the present mode of embodiment has been described. This is a continuous system as is plain from the description given above. It is optimum for the production of ethylene glycol on a commercial scale. Naturally, the production of this method may be carried out in a batch system.

Figure 2:
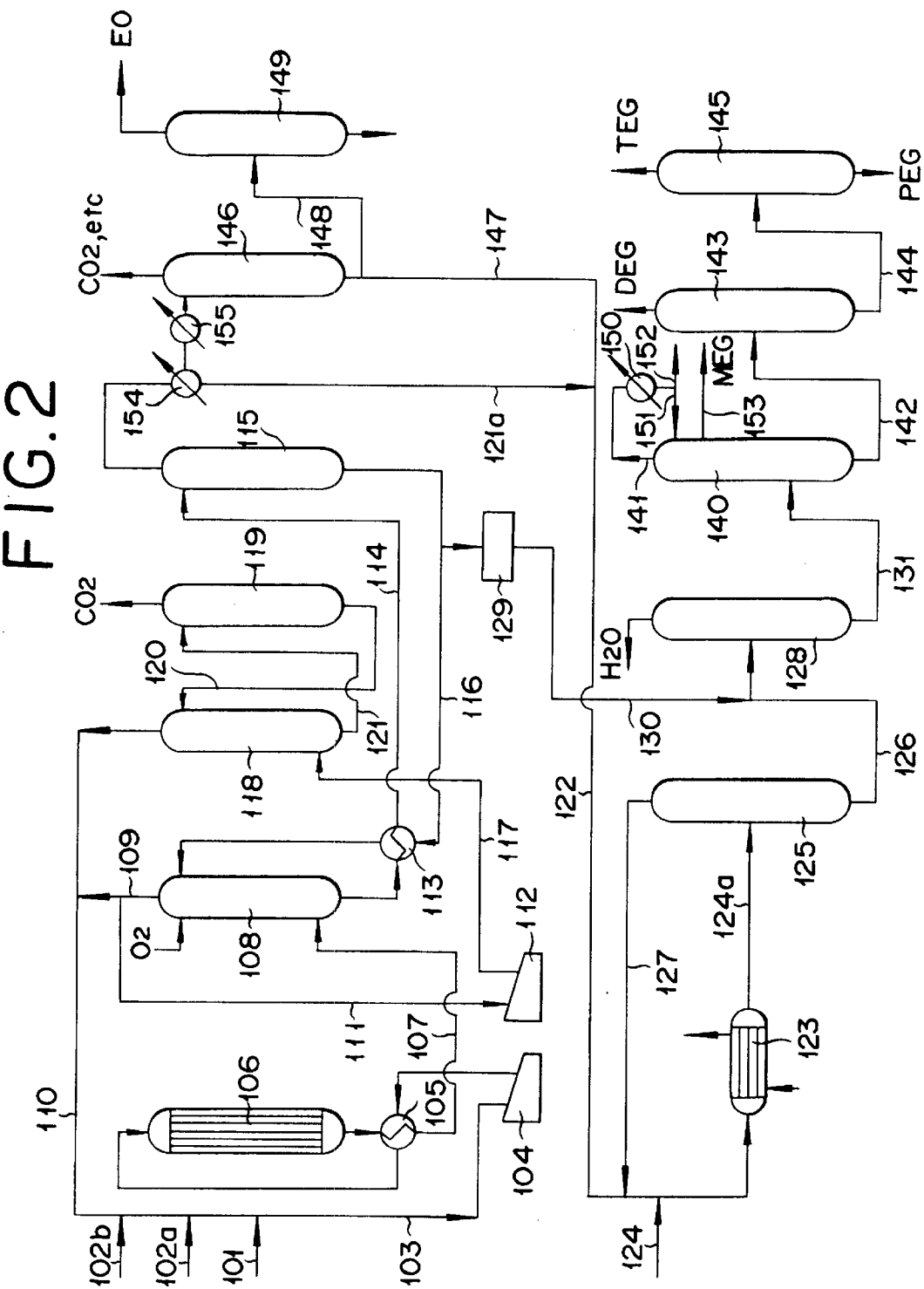
FIG. 2 is a flow sheet illustrating another example of the mode of embodying the method of this invention.

FIG. 2 illustrates another example of the mode of embodying the method of this invention. This mode of embodiment is identical with the mode of embodiment of FIG. 1 from the step of gas phase oxidation of ethylene through the step of hydration of ethylene oxide and the step of dehydration. In FIG. 2, therefore, the reference numerals which equal those of FIG. 1 plus 100 denote like members found in FIG. 1.

This invention, as illustrated in FIG. 2, contemplates introducing the side cut technique to the monoethylene glycol rectification column prior to producing monoethylene glycol by using ethylene oxide containing unpurified crude ethylene oxide as the raw material for a hydrric reaction, feeding an ethylene glycol solution containing practically no water (such as, for example, the bottom of a dehydration column)via a pipe 131 for feeding the ethylene glycol solution to a monoethylene glycol distillation column 140, subjecting the solution to distillation in the rectification column 140, condensing the vapor of monoethyllene glycol distilled out the top of the rectification column 140 wholly by a condenser 150 disposed on the route of a pipe 141 on the top part side, refluxing part of the monoethylene glycol solution to the rectification column 140 via a branched pipe 151 for rectification on the head part side, discharging out of the system the remaining contaminant-containing concentrated solution from the tower top part via a pipe 152, acquiring monoethylene glycol of high purity refluxed to the rectification column 140 as a product via a pipe 153 for side cut, and forwarding diethylene glycol and other high boiling components remaining in the bottom part of the rectification column 140 to an external diethylene glycol treating process via the pipe 142 on the column bottom side to be treated therein. Thus, the product of this operation can be separated into three components, i.e. (1) the column top condensate containing contaminants such as glycol aldehyde which have relatively low boiling components (light weight fractions), (2) the side cut solution of monoethylene glycol of high purity having a medium boiling component (intermediate fraction), and (3) the bottoms of the column such as diethylene glycol containing high boiling components (heavy weight fractions).

The alkaline substance may be added in the prescribed amount to the pipe 131 similarly in the mode of embodiment of FIG. 1.

Preferably in this invention, the bottoms of the monoethylene glycol dehydration column are fed to the monoethylene glycol distillation column and the distillation of the bottoms is carried out so that the cut ratio of the top part of the monoethylene glycol rectification column is not less than 0.01 wt. %, preferably in the range of 0.1–2 wt. % based on the amount of feed to the monoethylene glycol rectification column. By acquiring the monoethylene glycol emanating from the side cut part as a product and discharging out of the system the concentrated solution containing such contamintants as glycol aldehyde and emanating from the top part, the entrance of such contaminants into the side cut part can be prevented very effectively. If the cut ratio of the top part of the monoethylene glycol rectification column is less than 0.01 wt. % of the feed amount to the monoethylene glycol rectification column, the consequent decrease in the amount of the concentrated solution discharged out of the system from the top part of the monoethylene glycol rectification column will entail such disadvantages as preventing such contaminants as glycol aldehyde from being thoroughly transferred toward the concentrated solution side and eventually discharged, increasing the amount of the contaminants mingling as a foreign matter into the reflux solution refluxed from the top part, suffering the contaminants to mingle into the monoethylene glycol solution extracted from the side cut part, and inevitably bringing a reduction in the purity of the monoethylene glycol product. If the cut ratio of the top part of the monoethylene glycol rectification column exceeds 2 wt. % based on the amount of feed to the monoethylene glycol rectification column, the excess will entail such disadvantages as increasing the amount of monoethylene glycol in the concentrated solution discharged out of the system through the top part and lowering the ratio of acquisition of the monoethylene glycol product extracted from the side cut part. The expression "cut ratio of the top part of the monoethylene glycol rectification column" as used herein is to be defined as the weight percentage of the amount discharged out of the system from the column top part to the amount of feed to the column. The term "side cut technique" as used in the present specification refers generally to the technique which is applied to the distillation column for the purpose of separating the three-component system by distillation into a light weight fraction, an intermediate fraction, and a heavy weight fraction.

Now, the monoethylene glycol rectification column formed by the introduction of the side cut technique which is usable for this invention and the operation thereof and the conditions therefor will be explained below.

(1) Monoethylene Glycol Rectification Column (Hereinafter Referred to Briefly as "MEG Rectification Column")

Figure 3:
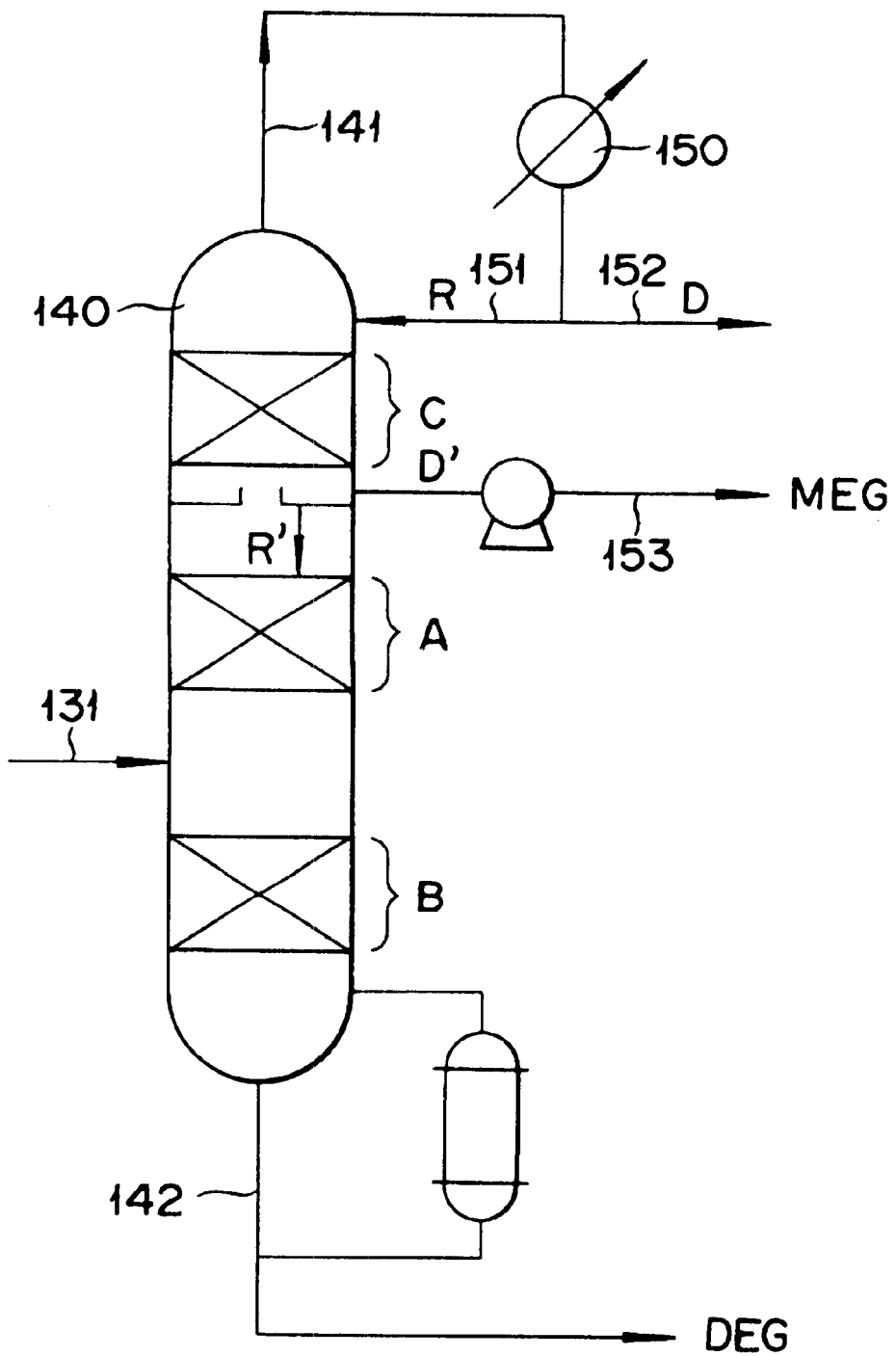
FIG. 3 is a flow sheet illustrating the details of a principal part of the method of FIG. 2.

The monoethylene glycol rectification column does not need to be particularly restricted as regards the type. Though it may be an ordinary distillation column, it is preferred to be a packed column which incurs pressure loss only sparingly. The conventional method of purification generally uses a complex column which is composed of one or two MEG rectification columns and a MEG stripper. The MEG rectification column is adapted for bottom feeding and possessed solely of a concentration part and the MEG recovery column forming the latter stage is adapted for intermediate level feeding and possessed of a recovery part. The MEG rectification column of this invention has only to be adapted for intermediate level feeding, constructed with a concentration part A and a recovery part B, and provided additionally on the concentration part mentioned above with a concentration part C intended exclusively for side cut as illustrated in FIG. 3. When the rectification is effected with a complex column as mentioned above, it suffices to have a concentration part for side cut installed on the concentration part with respect to at least one component column.

The working pressure of the monoethylene glycol rectification column is not particularly restricted but is properly decided depending on the temperatures of a heating source or a cooling source. Generally, it is in the range of 1–200 mmHg.

(2) Feed Solution to Monoethylene Glycol Rectification Column

In this invention, the feed solution directed to the monoethylene glycol rectification column is not particularly restricted but is only required to be such that the water content in the ethylene glycol solution fed to the monoethylene glycol rectification column is substantially zero (specifically not more than 0.1 wt. %). The bottom liquid of the monoethylene glycol dehydrating column which has the water content reduced substantially to zero in consequence of the treatment performed therein for the purpose of dehydration, for example, can be suitably utilized, though not exclusively. The bottom liquid, when necessary, may have been further treated with an alkali for the purpose of removing defiling substances as popularly practiced in the prior art.

The contaminant contained in the unpurified crude ethylene oxide to be used as the raw material for the hydration reaction includes aldehydes, organic chlorines, inorganic chlorines, and organic acids, depending on the history of the production the ethylene oxide. When this raw material, after having undergone the hydration reaction as expected, is subsequently in the process of ordinary dehydration, it is deprived of the greater part of such contaminant. The ethylene glycol solution eventually fed to the monoethylene glycol rectification column has incorporated therein glycol aldehyde which is separated by the ordinary operation of distillation with great difficulty and other unspecified trace defiling substance which is detrimental to thermal stability. In this invention, therefore, such defiling substances as glycol aldehyde which are separated from monoethylene glycol with extreme difficulty by the ordinary operation of distillation form the target of separation in the monoethylene glycol rectification column formed by the introduction of the side cut technique.

(3) Operating Conditions of Monoethylene Glycol Rectification Column

① The temperature of the top of the monoethylene glycol rectification column should not be uniquely defined because it is variable with the working pressure of the column. Though the range of the temperature of the top is inevitably suffered to widen extremely when the range of the working pressure defined above is taken into consideration, it is defined when forced at all to be in the range of 30°–160° C., preferably 85–125° C.

② The working pressure of the monoethylene glycol rectification column is as already defined above.

③ The ratio of the cut of the top part of the monoethylene glycol rectification column is likewise as already defined above.

④ The reflux ratio of the top part of the monoethylene glycol rectification column (R/D; refer to FIG. 3) is in the range of 10–500, preferably 100–400. It is commendable to decide this reflux ratio, depending on the theoretical number of steps and the amount of defiling substance.

⑤ The reflux ratio of the side cut of the monoethylene glycol rectification column (R'/D'; refer to FIG. 3) is in the range of 0.5–3, preferably 0.8–1.4. This R'/D' ratio has only to be decided likewise, depending on the number of steps of the concentration part so that the DEG concentration in the product falls within the specified range.

⑥ The theoretical number of steps of the concentration part of the monoethylene glycol rectification column (refer to FIG. 3) is in the range of 5–30, preferably 7–15. This theoretical number of steps may be decided in consideration of such factors as the composition of the feed so that the DEG concentration in the product falls within the specified range.

⑦ The theoretical number of steps of the concentration part for the side cut of the monoethylene glycol rectification column (refer to FIG. 3) is in the range of 3–10, preferably 5–10. It is commendable to decide this number properly depending on the amount of the defiling substance to be brought into the column.

In this invention, by introducing the side cut technique, it is made possible to have such defiling substances as glycol aldehyde mentioned above concentrated (possibly to 200–1000 times the original level under the operating conditions defined above) in the concentrated solution discharged from the top part of the monoethylene glycol rectification column. Though this column top liquid may be properly discarded outside the system, it is commendable to recover the column top liquid as an ethylene glycol-containing solution and put it to reuse in accordance with the method for the production of monoethylene glycol invented by the same inventors and applied separately for patent (specifically, a method for producing monoethylene glycol of high purity, characterized by using a recovered ethylene glycol-containing solution as a raw material, adding an alkali to the recovered ethylene glycol-containing solution, then subjecting it to a heat treatment, subsequently performing crude distillation thereon, and refining the produced monoethylene glycol). This reclamation heightens the ratio of the acquisition of monoethylene glycol to be produced from the whole plant.

This invention, owing to the introduction of the side cut technique, enables the whole side cut liquid of the monoethylene glycol rectification column to be recovered as a monoethylene glycol product of high purity in a high yield.

Now, this invention will be described more specifically below with reference to working examples.

EXAMPLE 1

As a unpurified crude ethylene oxide containing a chlorine compound, the vapor emanating from the top of an EO stripper was wholly obtained as condensed without being refluxed. The unpurified crude ethylene oxide was composed of 10 wt. % of ethylene oxide, 55 wt. ppm of impurities (including 2.8 wt. ppm of organic chlorine compound and 52 wt. ppm of aldehydes as reduced to acetaldehyde), and the balance of water. The unpurified crude ethylene oxide as the raw material for a hydration reaction was supplied to a pressure type reaction vessel and left reacting continuously therein under the conditions of 124° C. of inlet temperature, 165° C. of outlet temperature, and 2.5 MPa of inner pressure. Then, it was concentrated and dehydrated by the use of a quadruple effect evaporator can till a glycol concentration of 90 wt. %. The liquid in the final evaporator was forwarded to an ethylene glycol dehydration column, subjected to an operation of the column under a pressure of 70 mmHg, and dehydrated therein by distillation with the resultant steam expelled via the top of the ethylene glycol dehydration column. Meanwhile, the ethylene glycol solution was extracted through the bottom part of the ethylene glycol dehydration column and fed to a monoethylene glycol rectification column. During this feeding from the bottom part of the ethylene glycol dehydration column to the monoethylene glycol rectification column, potassium hydroxide was added to the ethylene glycol solution till a concentration of one atomic equivalent weight per one atom of inorganic chlorine generated in the solution. The inorganic chlorine content in the ethylene glycol was determined by analyzing a sample of the ethylene glycol solution extracted from the bottom part of the ethylene glycol dehydration column by means of ion chromatography. The pH of the feed solution to the monoethylene glycol rectification column determined by the use of the aqueous solution of a sample diluted with purified water to 50 wt. % was found to rise from 3.8 to a level in the range of 5.0–5.1. The ethylene glycol solution was purified in the monoethylene glycol rectification column and monoethylene glycol discharged by distillation through the top part of the rectification column was recovered. The monoethylene glycol thus obtained was tested for ethylene chlorohydrin concentration by the use of a gas chromatographic mass spectrometer (made by Shimadzu Seisakusho Ltd. and sold under the product code of "QP-5000"). Further, the monoethylene glycol was heated at 260° C. for 1 hour 10 minutes and then tested for transmittance to the ultraviolet ray at 220 nm by the use of an absorptiometer (made by Hitachi, Ltd. and sold under the product code of "U3200"). The results are shown in Table 1 below.

Control 1

In the same procedure as in Example 1, monoethylene glycol was purified in the monoethylene glycol rectification column without adding potassium hydroxide to a pipe for feeding the bottom liquid of an ethylene glycol dehydration column to the rectification column (consequently, the pH of the feed solution to the rectification column was not raised but was kept at 3.8). The produced monoethylene glycol was tested for ethylene chlorohydrin concentration by the gas chromatographic mass spectrometer (made by Shimadzu Seisakusho Ltd. and sold under the product code of "QP-5000"). Further, the produced monoethylene glycol was heated at 260° C. for one hour 10 minutes and then tested for the transmittance to the ultraviolet ray at 220 nm (made by Hitachi, Ltd. and sold under the product code of "U3200"). The results are shown in Table 1 below.

TABLE 1

|  | Example 1 | Control 1 |
| --- | --- | --- |
| Molar ratio of addition of potassium hydroxide (relative to the amount of inorganic chlorine in ethylene glycol solution) | 1:1 | None added |
| pH of feed solution to rectification column (determined of aqueous solution of sample diluted to 50 wt. % by addition of purified water) | 5.1 | 3.8 |
| Concentration of ethylene chlorohydrin in monoethylene glycol (ppm) | 0.1 | 3.1 |
| Transmittance to ultraviolet ray at 220 nm (%) of monoethylene glycol prior to heating | 85 | 85 |
| Transmittance to ultraviolet ray at 220 nm (%) of monoethylene glycol after heating | 85 | 69 |

EXAMPLE 2

AS the unpurified crude ethylene oxide, a crude ethylene oxide obtained by wholly condensing the top gas of a stripper without refluxing was used as the raw material for a hydration reaction. The raw material for the hydration reaction mentioned above and water added thereto were placed in a hydration reaction vessel and subjected therein to a hydration reaction. The product of this reaction was dehydrated in a plurality of distillation columns successively to expel low boiling components from monoethylene glycol to obtain a distillation column bottom liquid containing substantially no water. The bottom liquid was fed to the middle step of a monoethylene glycol rectification column formed by introducing the side cut technique. The distillation in the rectification column was carried out under the conditions of 127° C. of column top temperature, 60 mmHg of working pressure, and 0.56 wt. % of the cut ratio of the top part of the rectification column relative to the feed amount to the monoethylene glycol rectification column. The reflux ratio at the top part of the rectification column (R/D) was set at 144.9 and the reflux ratio at the side cut part of the rectification column (R'/D') at 1.6. The theoretical number of steps of the concentration part of the rectification column (refer to FIG. 3) was set at 7 and that of steps of the concentration part of the side cut of the rectification column (refer to FIG. 3) at 5. The monoethylene glycol obtained from the side cut part was acquired as a product and the concentrated liquid discharged through the top part was discharged out of the system. The produced monoethylene glycol product was tested for glycol aldehyde concentration by means of a liquid phase chromatograph (made by Shimadzu Seisakusho Ltd. and sold under the product code of "LC-10"). The results are shown in Table 2 below.

Further, the produced monoethylene glycol product was heated at 260° C. for 1 hour 10 minutes. When the monoethylene glycol product was tested for transmittance to the ultraviolet ray (UV 220 nm) before and after the heating, the transmittance was found to change from 85% before the heating to 84% after the heating. This result indicates that the transmittance showed practically no change before and after the heating and that the product had been thoroughly deprived of such substances as glycol aldehyde which were detrimental to thermal stability.

Control 2

The bottom liquid of a dehydration column containing practically no water similarly to the bottom liquid used in Example 2 was fed to the middle step of a monoethylene glycol rectification column which had not introduced the side cut technique and was distilled therein under the conditions of 127° C. of column top temperature and 60 mmHg of working pressure. Part of the monoethylene glycol obtained through the top part of the rectification column was refluxed at a reflux ratio of 1.6 and the remainder thereof were wholly acquired as a monoethylene glycol product. The theoretical number of steps of the concentration part of the rectification column was set at 7. The acquired monoethylene glycol product was tested for glycol aldehyde concentration. The results are shown in Table 2 below.

Further, the monoethylene glycol product thus obtained was heated at 260° C. for 1 hour 10 minutes. When it was tested for transmittance to the ultraviolet ray (UV 2200 nm) before and after the heating, the transmittance was found to change from 85% before the heating to 74% after the heating. The large decline of the transmittance after the heating indicates that the removal of the defiling substances detrimental to thermal stability was not sufficient.

TABLE 2

|  | Example 2 | Control 2 |
| --- | --- | --- |
| Point of acquisition of MEG product in the MEG rectification column | Side cut part | Column top |
| Concentration of GA in MEG product (ppm) | 0.2 | 3.7 |
| Transmittance to UV before heating (%) | 85 | 85 |
| Transmittance to UV after heating (%) | 84 | 74 |
| Ethylene chlorohydrin content (ppm) | 0.8 | 3.0 |

In Table 2 above, MEG stands for monoethylene glycol and GA for glycol aldehyde.

The entire disclosure of Japanese Patent Application Nos. 11-200898 and 11-200899 filed on Jul. 14, 1999, including specification, claims, summary and drawing are incorporated herein by reference in its entirety.

What is claimed is:

1. A method for production of monoethylene glycol of high purity, which comprises subjecting ethylene to catalytic vapor phase oxidation with a molecular oxygen-containing gas thereby obtaining an ethylene oxide-containing gas, exposing said ethylene oxide-containing gas to an absorbing solution thereby obtaining an ethylene oxide-containing solution, stripping said ethylene oxide-containing solution in a stripper, condensing the vapor consequently emanating from the top of said stripper thereby obtaining crude ethylene oxide, directly subjecting at least part of said crude ethylene oxide to a hydration reaction, adding an alkaline substance in an amount of not less than 0.5 atomic equivalent weight to the chlorine atom contained in the hydration reacted solution, and subjecting said resultant mixture to rectification.

2. A method according to claim 1, wherein said alkaline substance to be added is an oxide, a hydroxide, or a basic salt of an alkali metal or an alkaline earth metal.

3. A method according to claim 1, wherein the amount of said alkaline substance to be added is in the range of 0.5–2 atomic equivalent weight relative to one atom of the inorganic chlorine in the hydration reacted solution.

4. A method according to claim 1, wherein said unpurified crude ethylene oxide containing a chlorine compound is the ethylene oxide in the condensate obtained by cooling and/or absorbing the ethylene oxide-containing vapor emanating from the top part of the ethylene oxide stripper thereby condensing the vapor partly or wholly.

5. A method according to claim 1, wherein said unpurified crude ethylene oxide containing a chlorine compound is the condensate obtained by condensing partly or wholly the ethylene oxide-containing vapor emanating from the top part of the ethylene oxide stripper without refluxing said condensate to said stripper.

6. A method according to claim 1, wherein said unpurified crude ethylene oxide containing a chlorine compound is obtained by partly condensing the ethylene oxide-containing vapor emanating from the top part of the ethylene oxide stripper thereby obtaining a first condensate, leading the remainder of the uncondensed gas either in a further condensed state or in an unmodified state to the ethylene oxide dehydration column, and mixing the resultant dehydrated ethylene oxide with said first condensate.

7. A method according to claim 1, wherein the hydration reaction liquid is subjected to dehydration after adding alkaline substance, and further introducing a side cut technique to a monoethylene glycol rectification column, and aquiring monoethylene glycol from said side cut part.

8. A method for producing ethylene glycol of high purity, which comprises subjecting ethylene to catalytic vapor phase oxidation with a molecular oxygen-containing gas thereby obtaining an ethylene oxide-containing gas, exposing said ethylene oxide-containing gas to an absorbing solution thereby obtaining an ethylene oxide-containing solution, stripping said ethylene oxide-containing solution in a stripper, condensing the vapor consequently emanating from the top of said stripper thereby obtaining crude ethylene oxide, directly subjecting at least part of said crude ethylene oxide to a hydration reaction, removing water by distillation of the product of said hydration reaction, introducing the side cut technique to a monoethylene glycol rectification column, and acquiring monoethylene glycol from the side cut part.

9. A method according to claim 8, wherein the cut ratio of the top part of said monoethylene glycol rectification column is set at not less than 0.01 wt. % relative to the amount of feed to said monoethylene glycol rectification column.

10. A method according to claim 8, wherein said unpurified crude ethylene oxide is the ethylene oxide in the condensate obtained by cooling and/or absorbing the ethylene oxide-containing vapor emanating from the top part of the ethylene oxide stripper thereby condensing said vapor partly or wholly.

11. A method according to claim 8, wherein said unpurified crude ethylene oxide is the condensate obtained by condensing partly or wholly the ethylene oxide-containing vapor emanating from the top part of the ethylene oxide stripper without refluxing said condensate to said stripper.

12. A method according to claim 8, wherein said unpurified crude ethylene oxide is obtained by partly condensing the ethylene oxide-containing vapor emanating from the top part of the ethylene oxide stripper thereby obtaining a first condensate, leading the remainder of the uncondensed gas either in a further condensed state or in an unmodified state to the ethylene oxide dehydration column, and mixing the resultant dehydrated ethylene oxide with said first condensate.

* * * * *